United States Patent
Filippi et al.

(10) Patent No.: US 8,529,861 B2
(45) Date of Patent: *Sep. 10, 2013

(54) METHOD TO CARRY OUT STRONGLY EXOTHERMIC OXIDIZING REACTIONS IN PSEUDO-ISOTHERMAL CONDITIONS

(75) Inventors: Ermanno Filippi, Castagnola (CH); Enrico Rizzi, Casnate con Bernate (IT); Mirco Tarozzo, Ligornetto (CH); Keith A. Clayton, Strathmore (CA)

(73) Assignee: Ammonia Casale S.A. (CH)

( * ) Notice: Subject to any disclaimer, the term of this patent is extended or adjusted under 35 U.S.C. 154(b) by 1809 days.

This patent is subject to a terminal disclaimer.

(21) Appl. No.: 10/531,189

(22) PCT Filed: Sep. 8, 2003

(86) PCT No.: PCT/EP03/09931
§ 371 (c)(1),
(2), (4) Date: Oct. 6, 2005

(87) PCT Pub. No.: WO2004/035198
PCT Pub. Date: Apr. 29, 2004

(65) Prior Publication Data
US 2006/0140844 A1    Jun. 29, 2006

(30) Foreign Application Priority Data
Oct. 17, 2002 (EP) .................................. 02023316

(51) Int. Cl.
*C01B 21/38* (2006.01)
*F28F 27/02* (2006.01)

(52) U.S. Cl.
USPC ............ 423/392; 165/100; 165/157; 422/198

(58) Field of Classification Search
USPC ................. 422/192, 193, 198, 200, 211, 212, 422/216, 220, 222; 165/178
See application file for complete search history.

(56) References Cited

U.S. PATENT DOCUMENTS
6,153,149 A    11/2000   Rabitz et al.

FOREIGN PATENT DOCUMENTS
| EP | 1 236 505 A |   | 9/2002 |
| FR | 2029533 B1 | * | 10/1970 |
| GB | 391444 | * | 4/1933 |
| GB | 680 605 A |   | 10/1952 |

* cited by examiner

Primary Examiner — Melvin C Mayes
Assistant Examiner — Colin W Slifka
(74) Attorney, Agent, or Firm — Akerman Senterfitt

(57) ABSTRACT

Method and apparatus for carrying out highly exothermic catalyzed reactions, like so-called oxidative reactions, in pseudo-isothermal conditions, for example the reaction for producing nitric acid and the reaction for producing formaldehyde.

2 Claims, 2 Drawing Sheets

METHOD TO CARRY OUT STRONGLY EXOTHERMIC OXIDIZING REACTIONS IN PSEUDO-ISOTHERMAL CONDITIONS

FIELD OF THE INVENTION

In its most general aspect the present invention refers to a method for carrying out exothermic chemical reactions in pseudo-isothermal conditions.

In the rest of the description and in the subsequent claims, with the term pseudo-isothermal conditions we mean to indicate those conditions in which the reaction temperature is controlled in a limited range of values around a predetermined optimal value.

In particular, this invention concerns a method for carrying out, in pseudo-isothermal conditions, highly exothermic catalyzed reactions, like oxidative reactions, for example ammonia oxidation to give nitric acid and methanol oxidation to give formaldehyde.

The present invention also refers to an apparatus for carrying out the aforementioned method.

PRIOR ART

Regarding highly exothermic oxidative reactions it is well known that, in order to avoid clearly dangerous operating conditions, it is required to control one or more operating variables, like reaction temperature and concentration of at least one reactant.

Thus, for example, in the production of formaldehyde through methanol oxidation, the high concentration of the reactants and the high exothermicity of the reaction quickly lead to operate in explosive conditions; from here arises the need to strictly control both the concentration of the reactants and the reaction temperature below well-determined values.

Moreover, when the reaction temperature and concentration of the reactants exceed said values, there may happen phenomena of "poisoning" and degeneration of the catalyst, with the consequent inevitable yield reduction. This is the case of ammonia oxidation to give nitric acid, where the catalyst based upon $Co_3O_4$ undergoes a rapid CoO reduction, a much less active form of $Co_3O_4$, right when the concentration of the reactant exceeds a predetermined threshold at a predetermined temperature.

To control the temperature and the concentration of the reactants, it has been suggested to carry out the reactions of the considered type in fluid bed reactors.

This type of reactor, however, suffers from many recognized drawbacks, such as excessive energy consumption caused by the need to feed large quantities of air so as to keep the ammonia concentration below the explosivity threshold, greater constructive complexity with respect to fixed bed reactors and problems of dust recovery.

Moreover, the catalyst in movement inside said fluid bed reactors carries out a corrosive action against the walls of the reactors themselves.

SUMMARY OF THE INVENTION

The technical problem underlying the present invention is that of providing a method for carrying out highly exothermic oxidative reactions, in pseudo-isothermal conditions, between reactants fed in continuous flow to a predetermined catalytic bed, capable of overcoming the aforementioned drawbacks with reference to the prior art, in other words to operate below explosivity limits of the mixtures of reactants and of reactants-products and to promote a longer lifetime of the catalyst.

The aforementioned technical problem is solved, according to the present invention, by a method characterized in that at least part of said continuous flow of reactants is fed at different points of said catalytic bed corresponding to different successive stages of the reaction, at respective different predetermined temperatures and flow-rates, where the concentration of the reactants is low.

In the non-limiting case of use of a pseudo-isothermal reactor with a vertical axis, with a catalytic bed crossed axially by the reactants, the successive stages of the reaction are defined at different respective heights in the catalytic bed, wherein the reactants are fed at the predetermined flow-rates and temperatures.

The characteristics and advantages of the method of the present invention shall become clearer from the following description of an example embodiment thereof, made with reference to the attached drawings given for indicating and not limiting purposes.

DETAILED DESCRIPTION OF THE FIGURES

Figure 1:
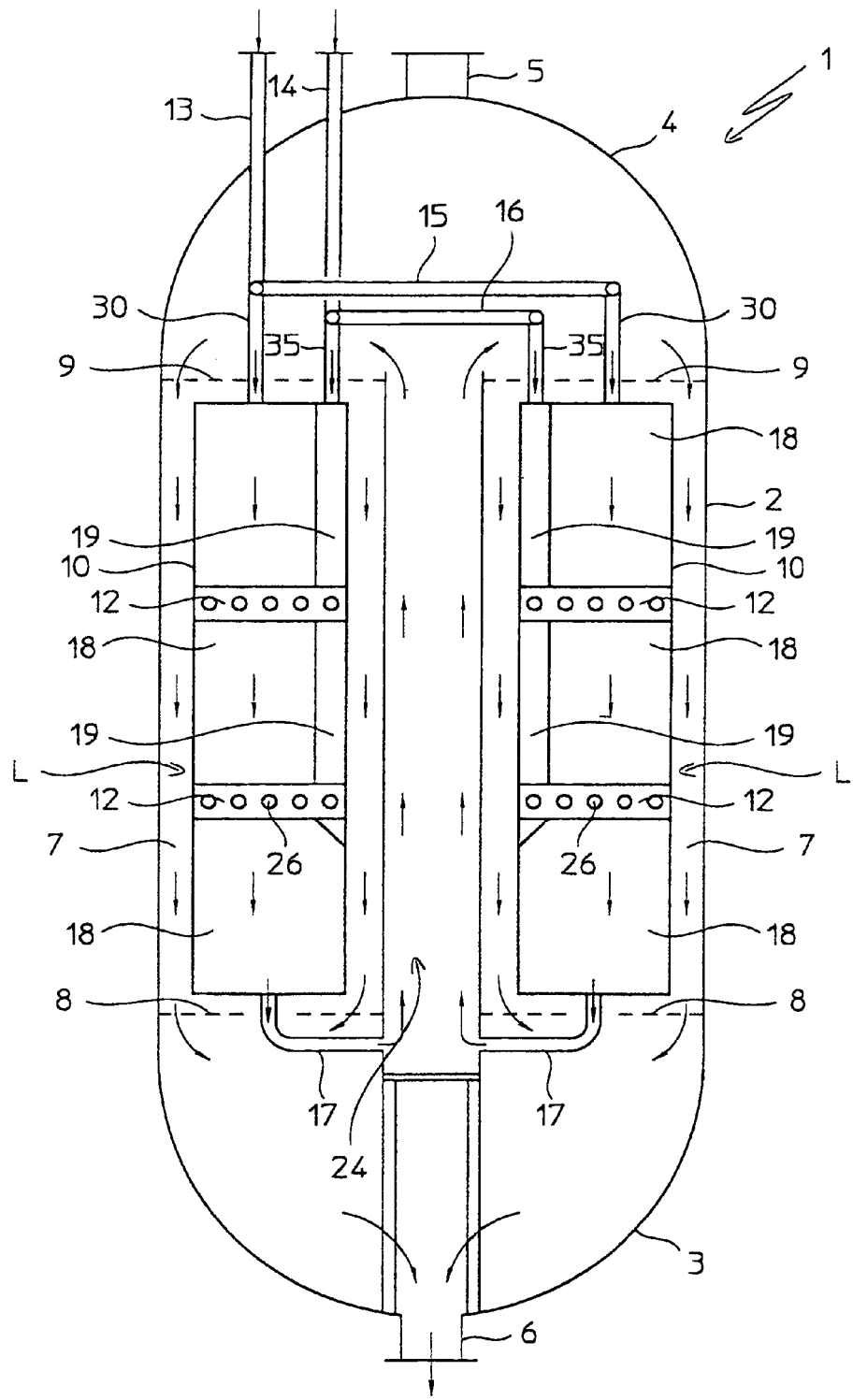
FIG. 1 schematically shows a chemical reactor for carrying out the method according to the invention.

With reference to FIG. 1, a chemical reactor, with a vertical axis, used to carry out highly exothermic reactions, for example and preferably oxidative reactions like ammonia oxidation to give nitric acid, is globally and schematically indicated with 1.

Said reactor 1 comprises a cylindrical shell 2, opposite end plates, lower 3 and upper 4. The upper end plate 4 is equipped with a manhole 5, whereas the lower end plate 3 is equipped with an opening 6 for discharging the reaction products.

In said shell 2 a reaction zone 7 is defined, representatively situated between a lower line 8 and an upper line 9, to receive a predetermined catalytic bed (L), intended to be crossed axially by the reactant gases and by the reaction products.

The catalytic bed (L) is supported in a per se known way and therefore it is not represented.

In the catalytic bed (L) a plurality of heat exchangers 10 and a corresponding plurality of distribution-supplier devices 12 are immersed and supported; said heat exchangers 10 are plate-shaped, rectangular, preferably arranged radially, in many rows concentric and coaxial to said shell and with long sides 11 parallel to the axis of the shell itself.

In accordance with a characteristic of the present invention, and according to a preferred embodiment, with each exchanger 10 is associated, in particular is fixed, a couple of distribution-suppliers 12, for which it constitutes an appropriate support, as shall become clear from the rest of the description.

Figure 2:
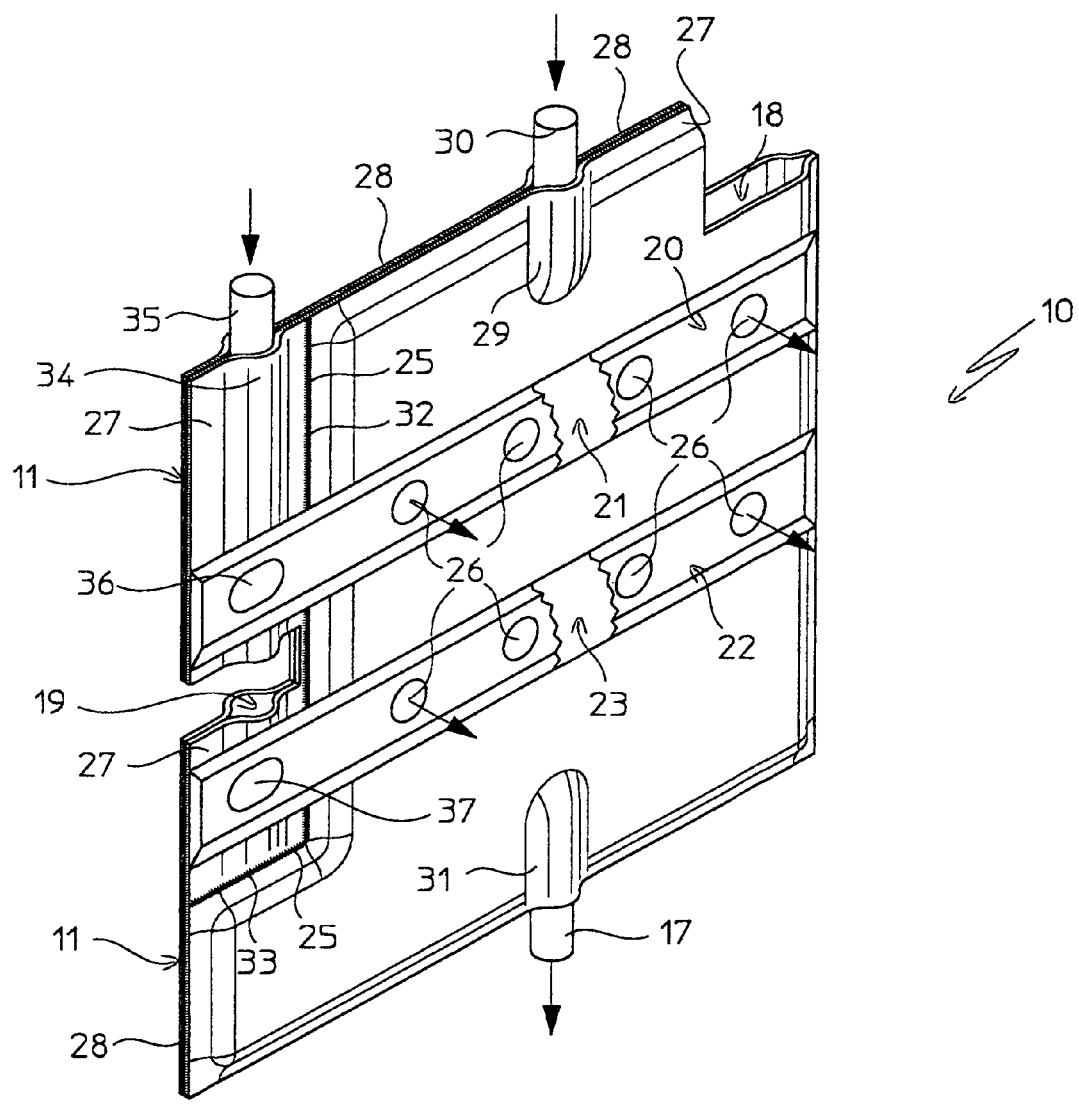
FIG. 2 schematically shows an enlarged view of a detail of the reactor of FIG. 1.

In particular, with reference to FIG. 2, each heat exchanger 10 comprises a wall 27 and a wall 28, juxtaposed, joined at the perimeter, for example through appropriate welding, in a mutually distanced relationship, so as to form a first chamber 18 between them.

Near to a side 11 of said exchanger 10 and through a welding line 25, having a portion 32 parallel to said side 11 and a portion 33 perpendicular to it, between said walls 27 and 28 a second chamber 19 is also defined, separated fluid-tight from said first chamber 18.

The chamber 18 is equipped with an inlet fitting 29, and with an outlet fitting 31, whereas the chamber 19 comprises only one inlet fitting 34.

Two box-shaped carters 20 and 22 are fixed to the wall 27 of each exchanger 10, extending perpendicularly to said side 11 for the whole width of the respective exchanger 10.

The carters 20 and 22 define with the wall 27 respective ducts 21 and 23, in fluid communication, on one side, with said second chamber 19 through openings 36 and 37, formed in the wall 27 and, on the other side, with the outside of the exchanger 10, and therefore with the catalytic bed (L) in which said exchanger 10 is immersed, through a plurality of holes 26, formed in the carters themselves.

Preferably, said holes 26 are arranged in rectilinear alignments, extending longitudinally to the respective carter (20, 22).

The carters 20 and 22, supported by a respective exchanger 10, essentially constitute a distribution-supplier device 12 for a predetermined fluid, fed to said carters through the chamber 18.

The plurality of exchangers 10 with relative distribution-suppliers 12, constitutes, in accordance with the present invention, an apparatus suitable for controlling the temperature and the concentration of the reactants in the catalytic bed (L), as shall become clear in the rest of the description.

The reactor 1 also comprises:
feed ducts for the predetermined reactants (13 and 14) which are in fluid communication with the chamber 18 and 19 respectively of each exchanger 10, through a system which includes ducts (15 and 16) and respective fittings (30 and 35).
collector ducts 17 for the reaction products, which are in fluid communication, on one side, with the outlet fittings 31 of each exchanger and, on the other side, with a central duct 24 axially provided in the reactor.

With reference to the aforementioned apparatus, the method of the present invention for carrying out highly exothermic oxidative reactions in pseudo-isothermal conditions, through simultaneous control of the reaction temperature and of the concentration of reactants around respective predetermined values, shall now be described.

A flow of reactants, for example ammonia and oxygen for the production of nitric acid, is continuously fed to the reactor 1, and is separated into two parts upon entry.

A first part or main part of said flow is preheated to the most appropriate temperature to trigger the desired reaction (ammonia oxidation) through heat exchange with the catalytic bed (L); for such a purpose and in the specific case illustrated, said main part of the flow of reactants is divided, through the distributor 12, between all of the ducts 15—fittings 30, for feeding the chambers 18 of all of the exchangers 10.

Exiting from the plurality of exchangers 10, the reactants thus preheated are collected by the collector 17, which conveys them to the lower end of the central duct 24. Exiting from the upper end of said duct 24, the preheated reactants are distributed above the catalytic bed (L), crossing which they start off the desired highly exothermic oxidation reaction.

A second part of said flow of reactants, or control flow, is divided between all the chambers 18 of the plurality of exchangers 10, from each of which it is fed to the respective pairs of distribution-suppliers 12.

As described above, said distribution-suppliers 12 are positioned in the catalytic mass of the bed (L), at heights strictly corresponding to the stages of the reaction taking place in correspondence of which it is foreseen to control the concentration and temperature of the reactants.

In accordance with the present invention such a control is substantially made possible by the injection in predetermined points of the catalytic bed of a fresh flow of reactants, the concentration of which is regulated continuously adjusting suitably and in a per se known way the flow rate of the second part of said flow of reactants.

The reaction products are discharged from the reactor 1 through the opening 6.

The invention thus conceived is susceptible to variants and modifications, all of which are covered by the scope of protection of the present invention defined by the following claims.

The invention claimed is:

1. A method for carrying out highly exothermic oxidative reactions in pseudo-isothermal conditions, between reactants fed in continuous flow to a predetermined catalytic bed, the method comprising:
   positioning a plurality of distribution-suppliers in said catalytic bed, at different points thereof strictly corresponding to different predetermined stages of said oxidative reaction,
   dividing said continuous flow of reactants into a first part or main flow and a second part or control flow with a predetermined temperature and flow-rate,
   preheating said first part or main flow through a plurality of heat exchangers immersed and supported in said catalytic bed,
   recovering said main flow of preheated reactants and feeding said main flow continuously to said catalytic bed, and
   feeding said second part or control flow to said plurality of distribution-suppliers to inject respective fresh flows of reactants at a predetermined temperature and flow-rate into the catalytic bed at different points of said catalytic mass corresponding to different successive stages of the reaction which takes place in said catalytic bed.

2. A reactor for carrying out a highly exothermic oxidative reaction in pseudo-isothermal conditions, comprising:
   a shell in which a reaction zone is defined;
   a catalytic bed at least partially occupying the reaction zone;
   a plurality of heat exchangers immersed in the catalytic bed; and
   a plurality of distribution-suppliers positioned in said catalytic bed at different points thereof corresponding to different predetermined stages of an oxidative reaction to be carried out in said reaction zone, at least one of said distribution-suppliers associated with each of said plurality of heat exchangers, said distribution-suppliers suitable for being fed continuously by a flow of reactants at a predetermined temperature and flow-rate, and for feeding said flow of reactants into a catalytic mass of said catalytic bed;
   wherein said heat exchangers are plate-shaped and substantially rectangular and define therein a first chamber, intended to be crossed by a respective flow of reactants to be preheated, and a second chamber, separated fluid-tight from said first chamber and in fluid communication with said at least one distribution-supplier, and
   wherein said at least one distribution-supplier is supported by a respective heat exchanger and comprises a carter fixed to a wall of said respective heat exchanger, with which it substantially defines a duct in fluid communication, on one side, with said second chamber of the exchanger and, on the other side, with the outside of the exchanger through a plurality of holes formed in said carter.

* * * * *